(12) United States Patent
Srinivasan et al.

(10) Patent No.: US 6,350,896 B1
(45) Date of Patent: Feb. 26, 2002

(54) PROCESS FOR PREPARATION OF AN ESTER USING A POLYANILINE SALT AS CATALYST

(75) Inventors: Palaniappan Srinivasan; Sairam Malladi, both of Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/813,097

(22) Filed: Mar. 20, 2001

(51) Int. Cl.⁷ .............................................. C07C 69/00
(52) U.S. Cl. ........................................ 560/129
(58) Field of Search .......................................... 560/129

(56) References Cited

U.S. PATENT DOCUMENTS 5,703,272 A * 12/1997 Abe et al. ................... 560/231

* cited by examiner

Primary Examiner—Gary Geist
Assistant Examiner—Taylor V Oh
(74) Attorney, Agent, or Firm—Ladas & Parry

(57) ABSTRACT

The invention relates to a process for preparation of an ester using a polyaniline salt as catalyst.

11 Claims, No Drawings

PROCESS FOR PREPARATION OF AN ESTER USING A POLYANILINE SALT AS CATALYST

FIELD OF THE INVENTION

The present invention relates to a process for the preparation of an ester using a polyaniline salt as the catalyst. The present invention more particularly relates to a process for producing aliphatic esters by the direct esterification of aliphatic mono carboxylic acids with aliphatic monohydric alcohols over polyaniline salts as catalysts.

BACKGROUND OF THE INVENTION

Esters are useful in a wide variety of industrial applications, such as for use in making coatings, adhesives, resins, fragrances, perfumes, plasticizers etc. Esterification is a well known equilibrium limited reaction involving reaction of a mono-, di- or polycarboxylic acid (or, in suitable cases, an acid anhydride) with an alcohol or phenol component. Such an alcohol or phenol component can be mono, di- or polyhydric.

Several synthetic routes exist to make esters, but most of them are not suitable to meet the stringent specifications which are being applied in the chemical industry. The most acceptable method of making an ester is to react an acid with an alcohol in the presence of catalyst.

Esterification is one of the most fundamental and important reactions in organic synthesis. Conventionally, the processes of making esters from acids and alcohols can be classified into the following three main categories: (R. C. Larock, Comprehensive Organic Transformations, VCH, New York, 1989, page 966, references therein, Encyclopedia of Chemical Technology, Vol 9, $4^{th}$ Edition, Wiley Interscience Publications, Page 755, references therein: Ullmann's Encyclopedia of Industrial Chemistry, Vol. 10, Vth Edition, 1987, Page 281, references therein; Vogel's, Text book of Practical Organic Chemistry, Longman Group Ltd., England, Vth Edition, 1996).

(a) Liquid-phase esterification reaction utilizing a liquid catalyst: This type of processes utilize liquid phase acid, such as sulfuric acid, phosphoric acid, sulfonic acid, or p-toluene sulfonic acid, as catalysts.

(b) Liquid phase esterification reaction utilizing a solid catalyst: This type of processes typically utilize inorganic salts, cationic ionic exchange resin and solid acid catalyst etc.

(c) Gas phase esterification reaction: This type of processes utilize a variety of catalysts such as heteropolyacids, liquid phase acids carried by a solid carrier, and zeolite in a gas phase reaction.

One of the problems associated with the liquid-catalyst liquid-phase esterification reaction is that the acidic liquid catalysts of sulfuric acid or p-toluene sulfonic acid cause corrosion in the reactor. These liquid acid catalysts are also discharged along with the reaction products, thus causing serious waste disposal and pollution problems. The drawbacks of using mineral acid as catalyst are: (i) Catalyst can not be reused, (ii) Disposal of acid is not environmentally safe and it is not economical, (iii) Low selectivity is frequently observed, (iv) Corrosion of the reaction vessel and reactors, (v) Not easy to handle and (iv) High inventory of the catalyst.

The solid-catalyst, liquid-phase esterification reaction, which typically utilizes a cationic ionic exchange resin as catalyst, ameliorates the corrosion and waste disposal problems experienced with the liquid-catalyst liquid-phase processes, and results in simplified separation procedure required between the reaction product and catalysts. However, cationic ion-exchange resins typically exhibit relatively poor heat-resistance, and they often lose substantial activity after being subject to heat. Once the catalytic activity of the cationic ion-exchange resins is reduced, it is difficult to be regenerated.

In the gas phase esterification reaction, the reaction conditions are maintained so that all the reactants and products are in the gas phase. Typically, inorganic materials are utilized as catalysts which typically exhibit excellent heat resistance and can be easily separated from the reaction products. However, the gas phase reaction necessitates a relatively large reaction vessel, resulting in large capital investment cost. Furthermore, if the gas phase esterification reaction is utilized to produce unsaturated carboxylic esters, the high reaction temperature often causes undesired by-products of polymers or oligomers to be produced. In certain instances, the high reaction temperature has caused the alcohol molecules to be dehydrated to become ethers. These side-reactions will tend to cause the reaction catalysts to lose their activity and result in operational difficulties.

OBJECTS OF THE INVENTION

The main object of the present is to provide a process for preparation of esters using polyaniline-salts as catalysts which obviates the drawbacks as detailed above.

It is another object of the invention to provide a process for the preparation of an ester which is environmentally safe.

It is a further object of the invention to provide a process for the preparation of an ester that allows catalyst recycling.

It is still another object of the invention to provide a process that is economical and efficient.

Another object of the present invention is to produce aliphatic esters by the direct esterification of aliphatic mono carboxylic acids with aliphatic monohydric alcohols over polyaniline salts as catalysts.

SUMMARY OF THE INVENTION

Accordingly, the present invention relates to a process for preparation of an ester said process comprising direct esterification of an aliphatic mono carboxylic acid with an aliphatic mono hydric alcohol in presence of a polyaniline salt catalyst at a temperature in the range of 40 to 80° C. for a time period in the range of 8 to 24 hrs. and separating the ester so obtained from the reaction mixture.

In one embodiment of the present invention, the aliphatic mono carboxylic acid used is selected from aliphatic mono carboxylic acids having C2–C20 carbon atoms.

In an another embodiment of the present invention, the aliphatic mono hydric alcohol used is selected from mono hydric alcohols having C1–C20 carbon atoms.

In a further embodiment of the invention, the aliphatic monohydric alcohol is selected from iso propyl alcohol and tertiary butyl alcohol.

In yet another embodiment of the present invention, the polyaniline salt catalyst used is selected from polyaniline-sulfate, polyaniline-hydrochloride, polyaniline-nitrate, polyaniline-p-toluene sulfonate and polyaniline-phosphoric acid salt.

In another embodiment of the invention the reaction is carried out in the temperature range of 70 to 80° C.

In yet another embodiment of the invention, the reaction is carried out for a period of 20 to 24 hrs.

In still another embodiment of the present invention, the catalyst amount used is in the range of 100 to 400 mg.

In yet another embodiment of the present invention, the amount of alcohol used is in the range of 1 ml to 5 ml.

DETAILED DESCRIPTION OF THE INVENTION

These embodiments will be apparent from the ensuing detailed description of the present invention.

The process of esterification may be carried out by reacting aliphatic mono carboxylic acid with aliphatic mono hydric alcohol in presence of catalyst, removing the catalyst by conventional methods. The ester can be isolated such as filtration followed by isolation of esters by conventional column chromatography using adsorbent such as silica gel and solvent such as chloroform, ethylacetate, hexane and mixture there off.

The following examples are given by way of illustration and therefore should not be construed as limit the scope of the present invention.

EXAMPLE 1

Three different methods were used to prepare polyaniline salts using three different oxidizing agents such as benzoyl peroxide, pyridinium chloro chromate and ammonium persulfate.

Method I: Preparation of polyaniline salts using benzoyl peroxide

In the polymerization process, 25 ml aqueous solution containing 1.44 g of sodium lauryl sulfate was added slowly while stirring to the solution of 150 ml dioxane containing 4.85 g benzoyl peroxide. In to this mixture, 30 ml aqueous solution containing 2.4 ml of aniline and 9 ml of concentrated sulfuric acid was added under constant stirring. The reaction mixture was stirred for 24 hrs at 30° C. The reaction mixture was filtered, washed with water and finally with acetone. The sample was dried at 100° C. till a constant weight. Using the same procedure, polyaniline-hydro chloride and polyaniline-nitrate salts were prepared using 9 ml hydrochloric acid and 6 ml nitric acid respectively instead of sulfuric acid.

Method 2: Preparation of polyaniline salts using pyridinium chloro chromate

In polymerization process, 1.0 ml of aniline and 3.0 ml of concentrated sulfuric acid were dissolved in 70 ml distilled water. To this solution, 25 ml aqueous solution containing 2.0 g of pyridinium chloro chromate was added drop wise (15–20 min. interval). The reaction mixture was stirred for 30 mins. at 30° C. The reaction mixture was filtered, washed with water and finally with acetone. The sample was dried at 100° C. till a constant weight. Using the same procedure, polyaniline-hydro chloride, polyaniline-nitrate, polyaniline-phosphate, polyaniline-p-toluene sulfonic acid salts were prepared using 9 ml hydrochloric, 6 ml nitric acid, 7 ml phosphoric, 2 g p-toluene sulfonic acid respectively instead of sulfuric acid.

Method 3: Preparation of polyaniline salts using ammonium persulfate

In polymerization process, 1.0 ml of aniline and 3.0 ml of concentrated sulfuric acid were dissolved in 70 ml distilled water. To this solution, 25 ml aqueous solution containing 2.3 g of ammonium persulfate was added dropwise (15–20 min. interval). The reaction mixture was stirred for 4 hrs. at 30° C. The reaction mixture was filtered, washed with water and finally with acetone. The sample was dried at 100° C. till a constant weight. Using the same procedure, polyaniline-hydro chloride, polyaniline-nitrate, polyaniline-phosphate, polyaniline-p-toluene sulfonic acid salts were prepared using 9 ml hydrochloric, 6 ml nitric acid, 7 ml phosphoric, 2 g p-toluene sulfonic acid respectively instead of sulfuric acid.

EXAMPLE 2

In a typical experiment, 1.0 g, of lauric acid was taken in 10 ml round bottom flask and 5.0 ml of methanol and 200 mg, of catalyst powder were added (method 1—polyaniline-sulfate salt). The reaction mixture was refluxed at 70° C. for different intervals of time. The reaction mixture was filtered and chloroform used to wash the mixture to recover the catalyst. The chloroform solvent and unreacted methanol were evaporated. The compound was loaded in a column containing silica gel of finer than 200 mesh. The product is eluted with 20:80 chloroform and hexane mixture using, 400 ml volume. The solvent mixture were recovered to (get the pure ester.

The yield of the ester prepared with different reaction time are given in Table 2.

| REACTION TIME (hrs.) | YIELD (%) |
| --- | --- |
| 4 | 1 |
| 8 | 63 |
| 12 | 80 |
| 16 | 88 |
| 20 | 99 |
| 24 | 99 |

EXAMPLE 3

In a typical experiment, 1.0 g of lauric acid was taken in 10 ml round bottom flask and 5.0 ml of methanol and different amount of catalyst powder was added (method 1—polyaniline-sulfate salt). The reaction mixture was refluxed at 70° C. for 24 hrs. The reaction mixture was filtered and chloroform used to wash the mixture in order to recover the catalyst. The chloroform solvent and unreacted methanol were evaporated. The compound was loaded in a column containing silica gel of finer than 200 mesh. The product is eluted with 20:80 chloroform and hexane mixture using, 400 ml volume. The solvent mixture were recovered to get the pure ester.

The yield of the ester prepared with different amount of catalyst are given in Table 3

| AMOUNT OF CATALYST (mg.) | YIELD % |
| --- | --- |
| 100 | 90 |
| 200 | 99 |
| 300 | 99 |
| 400 | 83 |

EXAMPLE 4

In a typical experiment, 1.0 g of lauric acid was taken in 10 ml round bottom flask and various amount of methanol and 200 mg of catalyst powder were added (method 1—polyaniline-sulfate salt). The reaction mixture was refluxed at 70° C. for 24 hrs. The reaction mixture was filtered and chloroform used to wash the mixture to recover the catalyst. The chloroform solvent and unreacted methanol were evaporated. The compound was loaded in a column containing silica gel of finer than 200 mesh. The product is eluted with 20:80 chloroform and hexane mixture using 400 ml volume. The solvent mixture were recovered to get the pure ester.

The yield of the ester prepared with different amount of methanol are given in Table 4.

| AMOUNT OF METHANOL (ml) | YIELD (%) |
|---|---|
| 1 | 55 |
| 2 | 90 |
| 3 | 92 |
| 4 | 99 |
| 5 | 99 |

EXAMPLE 5

In a typical experiment, 1.0 g of lauric acid was taken in 10 ml round bottom flask and 5.0 ml of methanol and 200 mg of catalyst powder was added (method 1—polyaniline-sulfate salt). The reaction mixture was refluxed at different temperatures for 24 hrs. The reaction mixture was filtered and chloroform used to wash the mixture to recover the catalyst. The chloroform solvent and unreacted methanol were evaporated. The compound was loaded in a column containing silica gel of finer than 200 mesh. The product is eluted with 20:80 chloroform and hexane mixture using 400 ml volume. The solvent mixture were recovered to get the pure ester.

The yield of the ester prepared with different temperatures are given in Table 5.

| TEMPERATURE (° C.) | YIELD % |
|---|---|
| 30 | 2 |
| 50 | 47 |
| 70 | 99 |

EXAMPLE 6

In a typical experiment, 1.0 g of lauric acid was taken in 10 ml round bottom flask and 5.0 ml of alcohol (different alcohols) and 200 mg of catalyst powder were added (method 1—polyaniline-sulfate salt). The reaction mixture was refluxed at 70° C. for 24 hrs. The reaction mixture was filtered and chloroform used to wash the mixture to recover the catalyst. The chloroform solvent and unreacted methanol were evaporated. The compound was loaded in a column containing silica gel of finer than 200 mesh. The product is eluted with 1:99 ethyl acetate and hexane mixture using 400 ml volume. The solvent mixture were recovered to get the pure ester.

The yield of the ester prepared with different alcohols are given in Table 6.

| ALCOHOL | YIELD (%) |
|---|---|
| Methanol | 99 |
| Ethanol | 95 |
| Propanol | 99 |

-continued

| ALCOHOL | YIELD (%) |
|---|---|
| Butanol | 99 |
| 1-dodecanol | 99 |
| Iso propyl alcohol | 26 |
| Tertiary butyl alcohol | 71 |

EXAMPLE 7

In a typical experiment, 1.0 g of acid (different acids) was taken in 10 ml round bottom flask and 5.0 ml of methanol and 200 mg of catalyst powder were added (method 1—polyaniline-sulfate salt). The reaction mixture was refluxed at 70° C. for 24 hrs. The reaction mixture was filtered and chloroform used to wash the mixture to recover the catalyst. The chloroform solvent and unreacted methanol were evaporated. The compound was loaded in a column containing silica gel of finer than 200 mesh. The product is eluted with 20:80 chloroform and hexane mixture using 400 ml volume. The solvent mixture were recovered to get the pure ester.

The yield of the ester prepared with different acids are given in Table 7.

| ACID | YIELD (%) |
|---|---|
| Caproic acid | 90 |
| Caprylic acid | 99 |
| Lauric acid | 99 |
| Myristic acid | 98 |
| Stearic acid | 99 |

EXAMPLE 8

In a typical experiment, 1.0 g of lauric acid was taken in 10 ml round bottom flask and 5.0 ml of methanol and 200 mg of catalyst powder (method 1—polyaniline-sulfate salt) were added. The reaction mixture was refluxed at 70° C. for 24 hrs. The reaction mixture was filtered and chloroform used to wash the mixture to recover the catalyst. The chloroform solvent and unreacted methanol were evaporated. The compound was loaded in a column containing silica gel of finer than 200 mesh. The product is eluted with 20:80 chloroform and hexane mixture using 400 ml volume. The solvent mixture were recovered to get the pure ester. The experiment was carried out six times using the recovered catalyst.

The yield of the ester prepared with recovered catalyst is given in Table 8.

| REPEATABILITY (no of times) | YIELD (%) |
|---|---|
| First | 99 |
| Second | 99 |
| Third | 99 |
| Fourth | 99 |
| Fifth | 99 |
| Sixth | 99 |
| Seventh | 99 |

EXAMPLE 9

In a typical experiment, 1.0 g of lauric acid was taken in 10 ml round bottom flask and 5.0 ml of methanol and 200 mg of catalyst powder (prepared by three different methods) were added. The reaction mixture was refluxed at 70° C. for 24 hrs. The reaction mixture was filtered and chloroform used to wash the mixture to recover the catalyst. The chloroform solvent and unreacted methanol were evaporated. The compound was loaded in a column containing silica gel of finer than 200 mesh. The product is eluted with 20:80 chloroform and hexane mixture using 400 ml volume. The solvent mixture were recovered to get the pure ester.

The yield of the ester prepared with different catalyst are given in Table 9.

| METHOD | POLYANILINE SALT | YIELD (%) |
| --- | --- | --- |
| I | Polyaniline-hydrochloride | 99 |
|  | Polyaniline-sulfate | 99 |
|  | Polyaniline-nitrate | 99 |
| II | Polyaniline-hydrochloride | 99 |
|  | Polyaniline-sulfate | 99 |
|  | Polyaniline-nitrate | 99 |
|  | Polyaniline-p-toluene sulfonic acid | 99 |
|  | Polyaniline-phosphoric acid salt | 65 |
| III | Polyaniline-hydrochloride | 99 |
|  | Polyaniline-sulfate | 99 |
|  | Polyaniline-nitrate | 99 |
|  | Polyaniline-p-toluene sulfonic acid | 99 |
|  | Polyaniline phosphoric acid salt | 75 |

The main advantages of the present invention are: the use of polyaniline-salts as catalysts in the liquid phase esterification of aliphatic mono carboxylic acids with aliphatic mono hydric alcohols for the first time. Also, the use of polyaniline salts as catalysts provides the following advantages compared with the use of other catalysts (i) high catalytic activity observed, (ii) catalyst do not corrode reaction vessel or reactors, (iii) repeated use of catalyst is possible, (iv) allowing recycling of catalyst, (v) separation of catalyst from a reaction mixture is easy and (vi) there is no problem for the disposal of used catalyst as they are environmentally safe, though the disposal of mineral acid catalyst requires much money for treatment to make it environmentally safe.

In view of the above, it will be seen that several advantages of the invention are achieved and other advantageous results attained. As various changes could be made in the above methods and compositions without departing from the scope of the invention, it is intended that all matter contained in the above description shall be interpreted as illustrative and not in a limiting sense.

We claim:

1. A process for preparation of an ester using a polyaniline salt as catalyst, said process comprising direct esterification of the corresponding aliphatic mono carboxylic acid with an aliphatic mono hydric alcohol in the presence of a polyaniline salt catalyst at a temperature in range of from 40 to 80° C. for a time period in the range of 8 to 24 hours, and separating the ester so obtained from the reaction mixture.

2. A process as claimed in claim 1, wherein the aliphatic monocarboxylic acid used is selected from an aliphatic monocarboxylic acid having 2 to 20 carbon atoms.

3. A process as claimed in claim 2, wherein the aliphatic monocarboxylic acid used is selected from caproic acid, caprylic acid, lauric acid, myristic acid, and steric acid.

4. A process as claimed in claim 1, wherein the aliphatic mono hydric alcohol used is selected from mono hydric alcohols having C1–C20 carbon atoms.

5. A process as claimed in claim 4 wherein the aliphatic mono hydric alcohol used is selected from methanol, ethanol, propanol, butanol, 1-dodecanol, iso propyl alcohol, and tertiary butyl alcohol.

6. A process as claimed in claim 1 wherein the polyaniline salt catalyst used is selected from polyaniline-sulfate, polyaniline-hydrochloride, polyaniline-nitrate, polyaniline-p-toluene sulfonate and polyaniline-phosphate salts.

7. A process as claimed in claim 1 wherein the reaction is carried out in the temperature from 70 to 80° C.

8. A process as claimed in claim 1 wherein the reaction is carried out for a period of 20 to 24 hrs.

9. A process as claimed in claim 1 wherein the catalyst amount used is 150 to 200 mg.

10. A process as claimed in claim 1 wherein the amount of alcohol used is 4 ml to 5 ml.

11. A process as claimed in claim 1 wherein the catalyst is reused for six times.

* * * * *